UNITED STATES PATENT OFFICE.

HOWARD W. FLAGG, OF YONKERS, NEW YORK.

FELTING FUR BODIES.

SPECIFICATION forming part of Reissued Letters Patent No. 11,213, dated December 22, 1891.

Original No. 444,209, dated January 6, 1891. Application for reissue filed August 17, 1891. Serial No. 402,940.

*To all whom it may concern:*

Be it known that I, HOWARD W. FLAGG, a citizen of the United States of America, and residing at Yonkers, county of Westchester, State of New York, have invented certain new and useful Improvements in Felting Fur Bodies, of which the following is a specification.

My invention relates to an improvement in felting fur bodies, and particularly fur hat-bodies.

Heretofore when it has been attempted to felt fur bodies alone in a fulling-mill, as is done with wool bodies, it has been found that under the action of the fulling-hammers the mass of fur bodies quickly packs so compactly that further pounding will injure or tear them. Though this could be avoided in part by removal from the mill and stretching and folding, they had to be handled so often that the process was troublesome and costly. This is largely due to the fact that fur, though of excellent felting qualities, is not sufficiently elastic.

The objects of my invention are to prevent the bodies from being thus packed and broken or injured during the felting process, and to do the work more economically than heretofore has been done.

With these objects in view my invention is a method of felting fur hats or other fur bodies, consisting in working them in a fulling-mill or other suitable device together with a suitable fibrous padding to give elasticity to the mass, preferably, but not necessarily, in the form of wool hat-bodies, which in this case would be felted at the same time.

I prefer to carry out my invention by placing, say, equal numbers of fur and wool hat-bodies together in a fulling-mill of any approved construction and felting the two kinds of bodies simultaneously, whereby the tender and inelastic fur hat-bodies are prevented from being packed down and torn or injured under the action of the hammers of the fulling-mill by the tougher and more elastic wool hat-bodies which form a padding for them. But for the padding action of the wool hat-bodies the fur hat-bodies would be torn or injured, and particularly when first placed in the mill, when they are very tender.

I have spoken of putting an equal number of fur and wool hat-bodies in the mill; but the percentage of each may be varied, as found desirable. The fur and wool hat-bodies are simply thrown into the mill together without any relative arrangement, and constantly shift about under the action of the hammers.

It is not essential that the protecting element in the mill be in the form of wool hat-bodies, for, if desired, other suitable fibrous bodies may be used in their stead. The padding is of fibrous material to secure flexibility and the quality of retaining the proper amount of moisture essential to the best results in felting, and to impart to the mass of bodies in the fulling-mill the requisite elasticity. By preference, however, I employ wool hat-bodies, as an obvious economy is secured by simultaneously felting the two kinds of hat-bodies in the same mill, and the wool hat-bodies, by reason of their shape, fibrous character, and elasticity, make an excellent padding.

My invention is not limited to fur hat-bodies, as other fur bodies may be felted in the same way.

Having fully described my invention, what I claim as new, and desire to secure by Letters Patent, is—

1. A method of felting fur bodies, consisting of working them in a fulling-mill together with other fibrous bodies employed in sufficient quantities to form a padding for them and prevent them from being injured or torn by the hammers of the fulling-mill, substantially as described.

2. A method of felting fur bodies, consisting in working them in a fulling-mill together with other elastic fibrous bodies employed in sufficient quantities to form a padding for them and prevent them from being injured or torn by the hammers of the fulling-mill, substantially as described.

3. A method of felting fur bodies, consisting in working them in a fulling-mill together with wool bodies employed in sufficient quantities to form a padding for them and prevent them from being injured or torn by the hammers of the fulling-mill, substantially as described.

4. A method of fur felting hat-bodies, consisting in working them in a fulling-mill simultaneously with wool hat-bodies employed in sufficient quantities to form a padding for the fur hat-bodies and prevent them from being torn or injured by the hammers of the fulling-mill, substantially as described.

Subscribed by me this 29th day of July, 1891, at Yonkers, county of Westchester, State of New York.

HOWARD W. FLAGG.

Witnesses:
THOMAS EWING, Jr.,
W. H. SCHULTZ.